United States Patent

Morgan et al.

[11] 3,976,619
[45] Aug. 24, 1976

[54] FLAME RETARDANT POLYMERS CONTAINING PHOSPHATES

[75] Inventors: Albert W. Morgan, Collinsville, Ill.; William Vanderlinde, St. Louis, Mo.

[73] Assignee: Monsanto Company, St. Louis, Mo.

[22] Filed: Dec. 5, 1974

[21] Appl. No.: 529,680

Related U.S. Application Data

[62] Division of Ser. No. 318,448, Dec. 26, 1972.

[52] U.S. Cl. .................... 260/45.7 P; 260/45.7 PS; 260/2.5 AJ
[51] Int. Cl.² ............................................ C08J 3/20
[58] Field of Search ............... 260/45.7 P, 45.7 PS, 260/928, 929, 965, 2.5 AJ

[56] References Cited
UNITED STATES PATENTS

| | | | |
|---|---|---|---|
| 2,782,128 | 2/1957 | Paist et al. | 260/929 |
| 3,157,613 | 11/1964 | Anderson et al. | 260/45.7 P |
| 3,321,555 | 5/1967 | Lutz et al. | 260/929 |
| 3,707,586 | 12/1972 | Turley | 260/45.7 P |
| 3,817,881 | 6/1974 | Turley | 260/45.7 P |

Primary Examiner—V.P. Hoke
Attorney, Agent, or Firm—Robert E. Wexler

[57] ABSTRACT

Compound of the formula

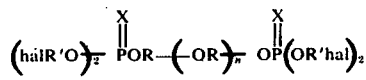

wherein R represents alkylene, cycloalkylene or alkylenecycloalkylene, R' represents an alkylene group of 1 to 10 carbons, X represents oxygen or sulfur, hal represents chlorine or bromine and $n$ represents an integer from 0 to 5, are useful as flame retardants for material and synthetic material.

9 Claims, No Drawings

FLAME RETARDANT POLYMERS CONTAINING PHOSPHATES

This application is a divisional application of Applicants' copending parent application Ser. No. 318,448, filed Dec. 26, 1972.

BACKGROUND OF THE INVENTION

This invention relates to novel flame retardant compounds, flame retardant resin compositions containing same and to a method for imparting flame resistance to natural and synthetic resins.

More particularly, this invention is directed to novel haloalkyl esters of glycols which have been found to impart flame resistance to a variety of polymeric materials.

Prior Art

Prior art which appears relevant to the present invention is as follows:

U.S. Pat. No. 2,978,478 discloses that alkylene glycols may be reacted with phosphorus compounds, such as phosphorus-oxychloride, to prepare phosphate esters. The reaction described in the patent is disclosed in the present invention as a method for preparing intermediate compounds which are subsequently converted to the novel flame retardant compounds of the present invention. The patent advises against preparing phosphate esters by the glycol/phosphorus oxychloride reaction since it is stated that heterocyclic esters will result therefrom, as well as the formation of diphosphate and polyphosphate esters. The patent does not disclose the compounds of the present invention.

U.S. Pat. No. 3,192,242 discloses certain bis (halomethyl)-1,3- propylenebis (phosphoroidihalidates) and reaction thereof with oxirane compounds to prepare flame retardant halogenated diphosphates. The haloalkyl glycol esters of the present invention are not shown.

U.S. Pat. No. 3,360,591 discloses chlorine-substituted aromatic esters of aromatic glycols which are used to reduce preignition of fuels. The compounds of the present invention are not disclosed.

Summary of the Invention

This invention relates to compounds of the formula

wherein R represents alkylene, cycloalkylene or bis (alkylene) cycloalkylene; R' represents an alkylene group of 1 to 10 carbon atoms; X represents oxygen or sulfur; hal represents chlorine or bromine and $n$ represents 1 when R is alkylene and a integer of from 0 to 5 when R represents cycloalkylene or alkylenecycloalkylene. The compounds of the invention have utility as flame retardant materials for resins.

The objective of this invention is to provide novel flame retardant materials to provide resin compositions containing same and to also provide a method for imparting flame retardance to resin systems.

DESCRIPTION OF THE PREFERRED EMBODIMENTS

The objective of this invention is accomplished by providing compounds of formula (I) above.

The novel compounds of the invention are prepared by reacting phosphoroldihalidates of glycols or glycol ethers having the formula

wherein R and $n$ are defined above with respect to Formula (I), with an oxirane compound.

Illustrative glycols which are utilized in the preparation of the compounds of the invention include alkylene glycols, cycloalkylene glycols, bis (alkylene) cycloalkylene glycols and alkylene glycol ethers. Illustrative alkylene glycols include alkylene glycols having from 1 to 10 carbon atoms, such as ethylene glycol, tetramethylene glycol, pentamethylene glycol, hexamethylene glycol, and decamethylene glycol.

Illustrative cycloalkylene glycols include cyclohexylene glycol (e.g. 1.4-cyclohexanediol) and cyclopentylene glycol and similar compounds.

Illustrative bis (alkylene) cycloalkylene glycols include bis (methylene) cyclohexylene glycol (e.g. 1,4-cyclohexane dimethylol), bis (ethylene) cyclohexylene glycol, bis (propylene) cyclohexylene glycol and like compounds.

Illustrative glycol ethers include diethylene glycol, dipropylene glycol and the like.

The preferred glycols and glycol ethers which are utilized to prepare the flame retardant materials of the present invention include diethylene glycol, ethylene glycol, cyclohexane dimethylol and cyclohexanediol.

The oxirane reactant which is utilized in the preparation of the compounds of the present invention include diethylene glycol, ethylene glycol, cyclohexane dimethylol and cyclohexane diol.

The oxirane reactant which is utilized in the preparation of the compounds of the present invention includes ethylene oxide, 1,2-propylene oxide, mixtures of ethylene oxide and propylene oxide, styrene oxide, epoxyalkanes such as 1,2-epoxybutane and the like.

The phosphorus oxyhalide or thiohalide reactant which is utilized in the preparation of the compounds of the present invention includes phosphorus oxytrichloride, phosphorus oxytribromide, phosphorus oxydibromidechloride and the corresponding thiophosphorus analogs.

Generally, the compounds of the invention are prepared by initially reacting the desired glycol with a phosphorus oxyhalide or phosphorus thiohalide to afford the intermediate glycol phosphorodihalidate or thiophosphorodihalidate, which is subsequently reacted with a oxirane compound to obtain the compounds of the invention.

The reaction conditions under which the compounds of the present invention are prepared are applicable to either batch or continuous operation. The temperature may be in the range of 0° to 100°C., with 40° to 60°C. preferable. Although the reaction may be run under a vacuum, a slight pressure (i.e. 2–20 psi) is preferable. Standard purification work-up procedures are used.

Fire retardant properties are afforded in natural and synthetic polymer materials by incorporating the compounds of the invention into such materials in an amount of from 1 to 100 phr (parts per hundred resin), preferably in an amount of from about 3 to about 20 phr.

The following examples illustrate specific embodiments of the preparation and utility of certain of the compounds of the present invention.

EXAMPLE 1

Preparation of diethylene glycol bis-phosphorodichloridate

In a 1 liter flask, fitted with a mechanical stirrer, thermometer and reflux condenser are placed 307 gms. (2.0 moles) phosphorus oxychloride. The phosphorus oxychloride is cooled to 14° to 15°C. and 106 gms. (1.0 moles) of diethylene glycol is added over a period of 2 to 3 hours. Residual phosphorus oxychloride is removed. The product recovered is is diethylene glycol bis-phosphorodichloridate. The temperature of the reaction mixture is then raised to 30°C. for about 1 hour.

EXAMPLE 2

Preparation of diethylene glycol bis-di-2-chloroethylphosphate

To the product of Example 1 there is added 2.5 gms. tetrabutyl titanate. Ethylene oxide is added subsurface at such a rate that the temperature is maintained at 65°–70°C. Completion of the reaction is indicated by the abrupt drop in temperature. The product is washed with sodium bicarbonate/water, dehydrated and filtered. The product is diethylene glycol bis-di-2-chloroethylphosphate. There is obtained 507 gms. (98 percent) of product.

EXAMPLE 3

Preparation of cyclohexane dimethylol-1,4-bis-phosphorodichloridate

In accordance with the procedure of Example 1, there are reacted one mole of cyclohexane dimethanol and two moles phosphorusoxychloride. The product is cyclohexane dimethylol-bis-phosphorodichloridate.

EXAMPLE 4

Preparation of cyclohexane dimethylol-bis-di-2-chloroethylphosphate

In accordance with the procedure of Example 2, tetrabutyl titanate is added to the product of Example 3 and ethylene oxide is introduced. The product is cyclohexane dimethylol-bis-di-2-chloroethylphosphate.

Following the procedure of Examples 1–4, but substituting phosphorus thiochloride for phosphorus oxychloride there is obtained diethylene glycol bis-thiophosphorodichloridate, diethylene glycol bis-di-2-chloroethylthiophosphate, cyclohexane dimethylol bis-thiophosphorodichloridate and cyclohexane dimethylol bis-di-2-chloroethylthiophosphate.

Substitution of propylene oxide for ethylene oxide in Examples 2 and 4 affords diethylene glycol bis-di-2-chloropropylphosphate and cyclohexanedimethylol bis-di-2-chloropropylphosphate.

EXAMPLE 5

Preparation of cyclohexanediol bis-phosphorodichloridate

In accordance with the procedure of Example 1, there are reacted one mole of 1,4-cyclohexanediol and two moles of phosphorus oxychloride to afford cyclohexanediol bis-phosphorodichloridate.

EXAMPLE 6

Preparation of cyclohexanediol-1,4-bis-di-2-chloroethylphosphate

In accordance with the procedure of Example 2, tetrabutyl titanate is added to the product of Example 5 and ethylene oxide is introduced. The product is cyclohexanediol-1,4-bis-di-2-chloroethylphosphate.

EXAMPLE 7

This example illustrates the flame retardant utility of the compounds of the present invention when incorporated in various resin composition.

A polymer composition is prepared having the following formulation:

| Substituent | Parts by Weight |
|---|---|
| "EPI-REZ"[1] | 70.0 |
| "VERSAMID"[2] | 30.0 |
| "MODAFLOW"[3] | 0.3 |
| Flame Retardant | 5, 10 or 20 |

[1]"EPI-REZ" 510 — epoxy resin presently available from Celanese Chemical Co.
[2]"VERSAMID" — polyamide stabilizer presently available from General Mills.
[3]"MODAFLOW" — processing aid presently available from Monsanto Company.

Three formulations are prepared, one being a control, the second containing a commercial flame retardant ("FYROL" 99, a trademark of Stauffer Chemical Co. for their brand of ethylene glycol polyphosphate flame retardant) and the third containing the compound of Example 2 of the invention. The comparative properties of the resins are shown in Table I, below. The "oxygen index" reflects data obtained in accordance with ASTM D2863-70 and is defined as the minimum concentration of oxygen, expressed as volume percent, in a mixture of oxygen and nitrogen that will just support combustion under the conditions of the test procedure. The greater the oxygen index, the better the flame retardancy.

Table I

| Flame Retardant | PHR* | Volatility, % Loss | Oxygen Index, % O$_2$ | % Soluble Mat. LOss | Water Extraction 48 Hrs. Drying & Absorption |
|---|---|---|---|---|---|
| Control | 0 | 0.11 | 17.9 | 0 | 1.89 |
| Ethylene glycol polyphosphate | 5 | 0.59 | 21.2 | 0 | 3.22 |
|  | 10 | 0.03 | 21.2 | 0.05 | 3.96 |
| Example 2 | 5 | 0.46 | 21.6 | 0 | 3.04 |

Table I-continued

| Flame Retardant | PHR* | Volatility, % Loss | Oxygen Index, % O$_2$ | % Soluble Mat. LOss | Water Extraction 48 Hrs. Drying & Absorption |
| --- | --- | --- | --- | --- | --- |
| Compound** | 10 | 0.03 | 21.3 | 0.56 | 4.12 |

* PHR—parts per hundred resin
** Diethylene glycol bis-di-2-chloroethyl phosphate The compound of Example 2 demonstrates improved flame retardance.

EXAMPLE 8

The compound of Example 2 is formulated, at 15 phr, into a flexible urethane foam having the following formulation:

| Substituent | Parts by Weight |
| --- | --- |
| Polyoxypropylene glycol | 100.00 |
| Triethylenediamine | 0.65 |
| Silicon surfactant | 1.00 |
| Water | 4.00 |
| Stannous octoate stabilizer | 0.16 |
| Tolylene diisocyanate | 54.00 |

The properties of the formulation are tested in comparison to a control containing no flame retardant and in comparison to the formulation containing 15 phr of a commercial flame retardant. The data are shown in Table II, below.

The column marked "ASTM-D-1962" in Table II refers to a horizontal burning test for cellular plastics. In such test, a specimen (6 inches × 2 inches × ½ inch) is supported on a horizontal, hard-cloth support with the ½ inch dimension vertical. One end of the specimen is contacted for 60 seconds with a 1½ inch high blue flame from a ⅜ inch diameter barrel Bunsen Burner fitted with a 1⅞ inch wide wingtop.

If the specimen instantly goes out, it is self-extinguishing. If the specimen burns and subsequently goes out, it is characterized as self-extinguishing/burn rate given as inches and seconds burned. If the specimen completely burns, its burn rate in inches/minute is given.

Table II

| Flame Retardant | Rate In./Min. | Self-Exting. In. | Self-Exting. Sec. | Fogging | Volatility % Loss |
| --- | --- | --- | --- | --- | --- |
| Control | 6.8 | — | — | 99 | 0.20 |
| Example 2 Compound | — | 0.5 | 10 | 89 | 0.77 |
| Ethylene glycol polyphosphate | — | 0.5 | 11 | 44 | 1.43 |

Fire retardants incorporated in flexible urethane foam are often so volatile as to be unusable in practical applications. In Table II the compound of Example 2 renders the foam self-extinguishing with only a slight increase in volatility. It also processes with no internal discoloration or scorch. Ethylene glycol polyphosphate has been found to scorch in this formulation and, while rated self-extinguishing, is twice as volatile as the compound of Example 2.

Results comparable to Examples 7 and 8 are obtained when the compounds of the present invention are incorporated in other resin systems, e.g. methacrylates, melamine/formaldehyde, vinyl halides and the like as described hereinafter.

As illustrated in Example 7 and 8, the compounds of the present invention are useful as flame retardants for a wide variety of natural and synthetic polymer materials. The compounds may be used in concentrations of from about 0.1 percent by weight of polymer up to about 50 weight percent or more depending on the particular use for which the polymer material is intended.

Synthetic polymer materials, i.e., those high molecular weight organic materials which are not found in nature, with which the compounds of the invention are advantageously employed may be either linear or cross-linked polymers and may be in the form of sheets, coatings, foams and the like. They may be either those which are produced by addition or condensation polymerization.

An important class of polymers which are beneficially flame retarded with the compounds of the invention are those obtained from a polymerizable monomer compound having ethylenic unsaturation. A particularly preferred class of polymers which are flame retarded consist of the polymerized vinyl and vinylidene compounds, i.e., those having the $CH_2 = C<$ radical. Compounds having such a radical are, for example, the solid polymeric alkenes, such as polyethylene, polypropylene, polyisobutylene or ethylene/propylene copolymers; polymerized acrylyl and alkacrylyl compounds such as acrylic, fluoroacrylic and methacrylic acids, anhydrides, esters, nitriles and amides, for example, acrylonitrile, ethyl or butyl acrylate, methyl or ethyl methacrylate, methoxymethyl or 2-(2-butoxyethoxy)ethyl methacrylate, 2-(cyanoethoxy)ethyl 3-(3-cyanopropoxy)propyl acrylate or methacrylate, 2-(diethylamino) ethyl or 2-chloroethyl acrylate or methacrylate, acrylic anhydride or methacrylic anhydride; methacrylamide or chloroacrylamide; ethyl or butyl chloracrylate; the olefinic aldehydes such as acrolein, methacrolein and their acetals; the vinyl and vinylidene halides such as vinyl chloride, vinyl fluoride, vinylidene fluoride and 1-chloro-1-fluoroethylene; polyvinyl alcohol; the vinyl carboxylates such as vinyl acetate, vinyl chloroacetate, vinyl propionate, and vinyl 2-ethylhexanoate; the N-vinyl imides such as N-vinyl phthalimide and N-vinyl succinamide; the N-vinyl lactams such as N-vinyl caprolactam and N-vinyl butyrolactam; vinyl aromatic hydrocarbon compounds such as styrene, alpha-methylstyrene, 2,4-dichlorostyrene, alpha- or beta-vinyl-naphthalene, divinyl benzene and vinyl fluorene; the vinyl ethers such as ethyl vinyl ether or isobutyl vinyl ether; vinyl-substituted heterocyclic compounds such as vinyl pyridine, vinyl pyrrolidone, vinylfuran or vinylthiophene; the vinyl or vinylidene ketones such as methyl vinyl ketone or isopropenyl ethyl ketone; vinylidene cyanide. Homopolymers of the above compounds or copolymers and terpolymers thereof are beneficially flame retarded by the compounds of the present invention. Examples of such copolymers or terpolymers are those obtained by polymerization of the following monomer mixtures; vinyl chloride/vinyl acetate, ethylene/vinyl chloride/vinyl acetate, acrylonitrile/vinyl pyridine, styrene/methyl methacrylate, styrene/N-vinyl pyrrolidone, cyclohexyl methacrylate/vinyl chloroacetate, acrylonitrile/vinylidene cyanide, methyl methacrylate/vinyl acetate, ethyl acrylate/methacrylamide/ethyl chloroacrylate, vinyl chloride/vinylidene chloride/vinyl acetate.

Other polymers of compounds having the ethylenic group, $>C=C<$, are homopolymers, copolymers and terpolymers of the alpha-, beta-olefinic dicarboxylic acids and derivatives thereof such as the ahydrides, esters, amides, nitriles and imides for example, methyl, butyl, 2-ethylhexyl or dodecyl fumarate or maleate; maleic chloromaleic, citraconic or itaconic anhydride; fumaronitrile, dichlorofumaronitrile or citracononitrile; fumaramide, maleamide or N-phenyl maleamide. Examples of particularly useful polymers and terpolymers prepared from the alpha-, beta- olefinic dicarboxylic compounds are the copolymers of maleic anhydride and a vinyl compound such as ethylene, propylene, isobutylene, styrene, alpha methylstyrene, vinyl acetate, vinyl propionate, methyl isopropenyl ketone, isobutyl vinyl ether, the copolymers of dialkyl fumarate such as ethyl or butyl fumarate and vinyl compounds such as styrene, vinyl acetate, vinylidene chloride, ethyl methacrylate, acrylonitrile and the like.

The compounds of the invention act as flame retardants for the polymers and copolymers of unsaturated, cyclic esters of carbonic acid, for example, homopolymeric vinylene carbonate or the copolymers of vinylene carbonate with ethylenic compounds such as ethylene, vinyl chloride, vinyl acetate, 1,3-butadiene, acrylonitrile, methacrylonitrile, or the esters of methacrylic or acrylic acid.

Readily flame retarded by the compounds of the invention are also the polyarylcarbonate polymers such as the linear polyarylcarbonates formed from diphenols or dihydroxy aromatic compounds including single and fused-ring nucleii with two hydroxy groups as well as monohydroxy-substituted aromatic residues jointly in pairs by various connecting linkages. Examples of the foregoing include dihydorxy benzenes, naphthalenes and the like, the dihydroxydiphenyl ethers, sulfones, alkanes, ketones and the like.

The compounds of the invention also act as flame retardants for polymers, copolymers or terpolymers of polymerizable compounds having a plurality of double bonds, for example, rubbery, conjugated diene polymerizates such as homopolymerized 3-butadiene, 2-chlorobutadiene or isoprene and linear copolymers or terpolymers such as butadiene/acrylonitrile, isobutylene/butadiene, butadiene/styrene; esters of saturated di- or poly-hydroxy compounds with olefinic carboxylic acids such as ethylene glycol dimethacrylate, triethylene glycol dicrotonate or glyceryl triacrylate; esters of olefinic alcohols with dicarboxylic acids or with olefinic monocarboxylic acids such as diallyl adipate, divinyl succinate, diallyl fumarate, allyl methacrylate or crotyl acrylate and other diethylenically unsaturated compounds such as diallyl carbonate, divinyl ether or divinylbenzene, as well as the crosslinked polymeric materials such as methyl methacrylate/diallyl methacrylate copolymer or butadiene/styrene/divinyl benzene terpolymer.

The cellulose derivatives are flame retarded by the compounds of the present invention. For example, cellulose esters such as cellulose acetate, cellulose triacetate or cellulose butyrate, the cellulose ethers such as methyl or ethyl cellulose, cellulose nitrate, carboxymethyl cellulose, cellophane, rayon, regenerated rayon and the like may be flame retarded.

The compounds of the present invention are well suited for flame retarding liquid resin compositions of the polyester type, for example, the linear polyesters which are obtained by the reaction of one or more polyhydric alcohols with one or more alpha, beta-unsaturated polycarboxylic acids alone or in combination with one or more saturated polycarboxylic acid compounds, or the crosslinked polyester resins which are obtained by reacting a linear polyester with a compound containing a $CH_2=C<$ group.

The compounds of the present invention are compatible flame retardants for epoxy resins. Such resins are condensation products formed by the reaction of a polyhydroxy compound and epichlorohydrin, which condensation products are subsequently cured by the addition of crosslinking agents. The hydroxy compounds may be, for example, ethylene glycol, 4,4'-isopropylidenediphenol and similar materials. The crosslinking agent employed in the curing step may be a dicarboxylic compound such as phthalic anhydride or adipic acid, but is more generally a polyamine such as ethylene diamine, paraphenylamine diamine or diethylene triamine.

Polyurethanes are a class of polymer materials which are flame retarded by the compounds of the present invention. The polyurethanes, like the above-mentioned polyesters, are materials which are employed in structural applications, for example, as insulating foams, in the manufacture of textile fibers, as resin bases in the manufacture of curable coating compositions and as impregnating adhesives in the fabrication of laminates of wood and other fibrous materials. Essentially, the polyurethanes are condensation products of a diisocyanate and a compound having a molecular weight of at least 500 and preferably about 1500–5000 and at least two reactive hydrogen ions. The useful active-hydrogen containing compounds may be polyesters prepared from polycarboxylic acids and polyhydric alcohols, polyhydric polyalkylene ethers having at least two hydroxy groups, polythioether glycols, polyesteramides and similar materials.

The polyesters or polyester amides used for the production of the polyurethane may be branched and/or linear, for example, the esters of adipic, sebasic, 6-aminocaproic, phthalic, isophthalic, terephthalic, oxalic, malonic, succinic, maleic, cyclohexane-1,2-dicarboxylic, cyclohexane-1,4-dicarboxylic, polyacrylic, naphthalene-1,2-dicarboxylic, fumaric or itaconic acids with polyalcohols such as ethylene glycol, diethylene glycol, pentaglycol, glycerol, sorbitol, triethanolamine and/or amino alcohols such as ethanolamine, 3-aminopropanol, and with mixtures of the above polyalcohols and amines.

The alkylene glycols and polyoxyalkylene or polythioalkylene glycols used in the production of polyurethanes may be ethylene glycol, propylene glycol, butylene glycol, diethylene glycol, triethylene glycol, polythioethylene glycol, dipropylene glycol and the like.

Generally, any of the polyesters, polyisocyanate-modified polyesters, polyester amides, polyisocyanate-modified polyester-amines, alkylene glycols, polyisocyanate-modified alkylene glycols, polyoxyalkylene glycols and polyisocyanate-modified polyoxyalkylene glycols having three reactive hydrogen atoms, three reactive carboxylic and/or especially hydroxyl groups may be employed in the production of polyurethanes. Moreover, any organic compound containing at least two radicals selected from the group consisting of hydroxy and carboxy groups may be employed.

The organic polyisocyanates useful for the production of polyurethanes include ethylene diisocyanate, ethylidene diisocyanate, propylene-1,2-diisocyanate, m-phenylene diisocyanate, 2,4-tolylene diisocyanate, triphenylmethane triisocyanate, or polyisocyanates in blocked or inactive form such as the bis-phenyl carbamates of tolylene diisocyanate and the like.

Phenolic resins are flame retarded by the compounds of the present invention, which compounds may be incorporated into the phenolic resin either by milling and molding applications or by addition to film-forming or impregnating and bonding solutions prior to casting. Phenolic resins with which the present compounds are employed are, for example, the phenol-aldehyde resins prepared from phenols such as phenol, cresol, xylenol, resorcinol, 4-butylphenol, cumylphenol, 4-phenylphenol, -nonylphenol, and aldehydes such as formaldehyde, acetaldehyde or butyraldehyde in the presence of either acetic or basic catalysts, depending upon whether the resin is intended for use as a molding or extruding resin or as the resin base in coating and impregnating compositions.

Aminoplasts are another group of aldehyde resins which are flame retarded by the compounds of the invention. Examples of aminoplasts are the heat-convertible condensation products of an aldlehyde with urea, thiourea, quanidine, cyanamide, dicyandiamide, alkyl or aryl guanamines and the triazines such as melamine, 2-fluoro-4,6-diamino-1,3,5-triazine and the like. When the aminoplasts are to be used as impregnating agents, bonding adhesives, coatings and in casting of films, the compounds of the present invention are incorporated into solutions or suspensions in which the aminoplast is carried. The resulting mixtures give strong, fire-retardant laminates when sheets of paper, glass, cloth or fabric are impregnated therewith and cured.

Another class of compounds which are flame retarded by compounds of the present invention are the nylons, for example, the superpolyamides which are generally obtained by the condensation of a diamine, for example, hexamethylene diamine with a dicarboxylic acid, for example, adipic acid.

Other polyamides which are flame retarded in accordance with the present invention are the polypeptides which may be prepared, for example, by reaction of N-carbobenzyl oxyglycine with glycine or mixture of glycine and lysine or an N-carboxy amino acid anhydride such as N-carboxy-DL-phenylalanine anhydride, piperidone, 2-oxohexamethyleneimine and other cyclic amides. The compounds of the present invention can be incorporated into molding or extruding compositions for a flame retardant effect.

The compounds of the present invention are also useful as flame retardants for linear polymers obtained by the self-condensation of bifunctional compounds, for example, the polyethers which are derived by the self-condensation of dihydric alcohols such as ethylene glycol, propylene glycol or hexamethylene glycol; the polyesters which are obtained by the self-condensation of hydroxy acids such as lactic acid or 4-hydroxybutric acid; the polyamides which are prepared by the self-condensation of aminocarboxylic acids such as 4-aminobutyric acid; the polyahydrides which are formed by the self-condensation of dicarboxylic acids such as sebasic or adipic acid.

The preferred synthetic polymer materials which are flame retarded by the compounds of the present invention are the vinyl halide polymers in the form of milled products, plastisols and foams, rigid and flexible polyurethane coatings and foams, epoxy resins, ABS and GRS rubbers, aminoplasts and phenolics. The vinyl halide polymers can be simple, mixed homopolymers of vinyl chloride or polyvinylidene chloride, or copolymers or terpolymers in which the essential polymeric structure of polyvinyl chloride is interspersed at intervals with residues of other ethylenically unsaturated compounds copolymerizable therewith. The essential properties of the polymeric structure of polyvinyl chloride is retained if not more than about 40 percent of a comonomer is copolymerized therewith. Especially preferred copolymers include ethylene/vinyl chloride and vinyl chloride/acrylonitrile copolymers. Especially preferred terpolymers include ethylene/vinyl chloride/acrylonitrile, ethylene/vinyl chloride/acrylic acid and ethylene/vinyl chloride/acrylamide terpolymers.

Natural polymeric materials which may be flame retarded by the compounds of the present invention include natural rubber, cellulose esters, for example, cellulose acetate and cellulose nitrate, ethyl cellulose, cork and wood flour products and similar cellulosic materials.

The polymer formulations which are flame retarded in accordance with the present invention, whether in sheet or film form or of foam or molded structure, may contain various conventional additives such as fillers, extenders, crosslinking agents and colorants. Minor amounts of stabilizers, for example, are usually incorporated to reduce the effects of heat and light.

When foamable compositions are used, the composition may be a self-blowing polymer or the polymer may be blown by chemical or mechanical means or by the use of compressed gas. Fillers which are frequently employed to lower the cost of the finished material and to modify its properties include calcium carbonate and magnesium silicate. When fillers are employed, they are generally present in an amount of up to about 150 parts by weight of filler per 100 parts by weight of polymer formulation.

Where a colored or tinted composition is desired, colorants or color-pigments are incorporated in amounts of from about one to about five parts by weight to 100 parts by weight of polymer.

Surfactants such as silicones are normally added to foam formulations which are mechanically frothed. The surfactants reduce the surface tension of the foam and thereby increase the air or gas entrapment characteristics of the foam.

Additionally, glass-forming inorganic materials such as zinc borate, zinc oxide, lead oxide, lead silicate and silicon dioxide may be added to decrease the flame and smoke generating characteristics of the polymer.

While the invention has been described by referring to certain specific embodiments, it is not so limited since many modifications and variations are possible in the light of the above teachings. The invention may therefore be practiced otherwise than as specifically described without departing from the spirit and scope of the invention.

The embodiments in which an exclusive property or privilege is claimed are defined as follows:

1. A polymer composition containing an effective flame retardant amount of a compound of the formula

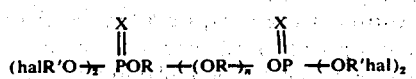

wherein R represents cycloalkylene or alkylenecycloalkylene of from 5 to about 12 carbon atoms, R' represents an alkylene group of 2 to 10 carbon atoms, X represents oxygen or sulfur, hal represents chlorine or bromine and $n$ represents an integer from 0 to 5.

2. A polymer composition of claim 1 wherein said compound is cyclohexane dimethylol bis-di-2-chloroethyl phosphate.

3. A polymer composition of claim 1 wherein R represents cycloalkylene and $n$ is 0.

4. Composition of claim 1 wherein said polymer is an epoxy resin.

5. Composition of claim 1 wherein said polymer is a flexible urethane foam.

6. Composition of claim 1 wherein said polymer is a methacrylate polymer.

7. Composition of claim 1 wherein said polymer is a melamine/formaldehyde resin.

8. Composition of claim 1 wherein said polymer is a vinyl halide polymer.

9. A polymer composition of claim 8 wherein said compound is cyclohexanediol bis-di-2-chloroethyl phosphate.